(12) United States Patent
Stubbs et al.

(10) Patent No.: US 7,373,200 B2
(45) Date of Patent: May 13, 2008

(54) SYSTEM AND METHOD FOR PROVIDING TACHYARRHYTHMIA THERAPY BY IMPLANTABLE DEVICE IN PRESENCE OF SYSTEM FAULTS

(75) Inventors: Scott Stubbs, Maple Grove, MN (US); Conrad L. Sowder, Minneapolis, MN (US); William J. Linder, Golden Valley, MN (US); Lynn S. Elliott, Maple Grove, MN (US); Kenneth P. Hoyme, Plymouth, MN (US); Hiten J. Doshi, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 300 days.

(21) Appl. No.: 11/122,970

(22) Filed: May 5, 2005

(65) Prior Publication Data

US 2006/0253158 A1 Nov. 9, 2006

(51) Int. Cl.
*A61N 1/39* (2006.01)
(52) U.S. Cl. .............................. 607/5; 607/27; 607/63
(58) Field of Classification Search ................ 607/3–5, 607/63, 27, 14, 29, 9
See application file for complete search history.

(56) References Cited

U.S. PATENT DOCUMENTS

| | | | |
|---|---|---|---|
| 4,164,946 A | * | 8/1979 | Langer ........................ 607/27 |
| 5,571,141 A | * | 11/1996 | McNeil et al. .................. 607/5 |
| 5,735,882 A | | 4/1998 | Rottenberg et al. |
| 6,128,528 A | | 10/2000 | Erickson et al. |
| 6,128,530 A | * | 10/2000 | Galen et al. .................... 607/5 |
| 6,198,968 B1 | | 3/2001 | Prutchi et al. |
| 6,584,355 B2 | | 6/2003 | Stessman |
| 6,635,048 B1 | | 10/2003 | Ullestad et al. |
| 2002/0032470 A1 | | 3/2002 | Linberg |
| 2003/0036776 A1 | | 2/2003 | Foster et al. |
| 2003/0135244 A1 | | 7/2003 | Esler |
| 2003/0176894 A1 | | 9/2003 | Stahmann et al. |
| 2004/0138724 A1 | | 7/2004 | Sieracki et al. |

FOREIGN PATENT DOCUMENTS

EP 0753327 A2 1/1997

* cited by examiner

*Primary Examiner*—Kennedy Schaetzle
(74) *Attorney, Agent, or Firm*—Schwegman, Lundberg & Woessner, P.A.

(57) ABSTRACT

A system and method is disclosed by which an implantable cardiac device may deliver tachyarrhythmia therapy in the event of a system fault. A hardware-based safety core provides the logic circuitry for detecting tachyarrhythmias and delivering shock therapy in the event of a fault which disables operation of the device's primary control circuitry. The safety core defibrillator eliminates common mode failure of the primary control circuits used in the primary defibrillator system. Failures in the primary controller memory or execution will activate the safety core defibrillator.

19 Claims, 4 Drawing Sheets

SYSTEM AND METHOD FOR PROVIDING TACHYARRHYTHMIA THERAPY BY IMPLANTABLE DEVICE IN PRESENCE OF SYSTEM FAULTS

CROSS REFERENCE TO RELATED APPLICATIONS

This application is related to the following co-pending applications both of which were filed on May 5, 2005, and are hereby incorporated by reference in their entirety: "SYSTEM AND METHOD FOR PROVIDING BRADYCARDIA THERAPY BY IMPLANTABLE DEVICE IN PRESENCE OF SYSTEM FAULTS", Ser. No. 11/122,982, and "SYSTEM AND METHOD FOR RECOVERING FROM TRANSIENT FAULTS IN AN IMPLANTABLE MEDICAL DEVICE", Ser. No. 11/123,246.

FIELD OF THE INVENTION

This invention pertains to systems and methods for operating implantable medical devices.

BACKGROUND

Cardiac rhythm management devices (CRMDs) are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy may also be delivered for the purpose of restoring synchronous ventricular contractions in patients with inter-ventricular or intra-ventricular conduction disorders, termed cardiac resynchronization therapy. Other cardiac rhythm management devices are designed to detect atrial and/or ventricular tachyarrhythmias and deliver electrical stimulation in order to terminate the tachyarrhythmia in the form of a cardioversion/defibrillation shock or anti-tachycardia pacing. Certain combination devices may incorporate any or all of the above functionalities.

CRMD's are complex electronic devices which are subject to failures of various kinds after implantation. It is desirable for such devices to be able to detect when these failures occur and then take action which minimizes harm to the patient.

SUMMARY

A system and method is disclosed by which an implantable cardiac device may deliver tachyarrhythmia therapy in the event of a system fault. A hardware-based safety core provides the logic circuitry for detecting tachyarrhythmias and delivering shock therapy in the event of a fault which disables operation of the device's primary control circuitry. The safety core defibrillator eliminates common mode failure of the primary control circuits used in the primary defibrillator system. Failures in the primary controller memory or execution will activate the safety core defibrillator.

DETAILED DESCRIPTION

Figure 1:
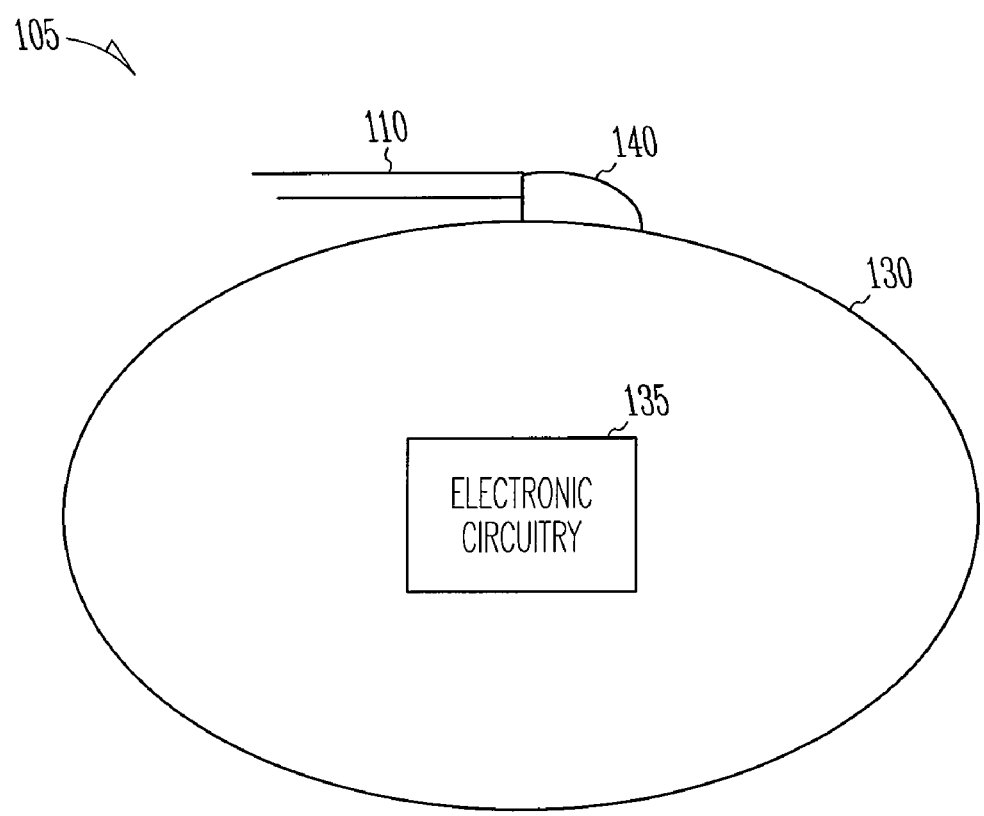
FIG. 1 illustrates the physical configuration of an exemplary implantable device.

Implantable cardiac rhythm management devices are usually microprocessor-based devices whose normal operation can be disrupted by fault events, either arising from a hardware failure or a software problem. The disruption in normal operation, if left unchecked, could cause the device to behave in way which is unsafe for the patient. It is common for CRMD's to incorporate fault detection circuitry which, upon detecting a fault, causes the device to enter a state which is expected to be safe for the patient. For example, a watchdog timer is a hardware timer which runs continuously and is reset periodically by the main control software of the CRMD during normal operation. If a fault disrupts normal operation of the main control software (e.g., a software crash), however, the watchdog timer is allowed to time out and generate a reset signal which re-initializes the system or causes the device to revert to specified operating state. Reset and recovery mechanisms in low-power medical devices historically have been ad hoc designs, attempting to provide limited recovery mechanisms in response to specific fault conditions. These mechanisms can be complex to get to work correctly, and do not effectively respond to unanticipated fault conditions.

In contradistinction to previous systems which employ ad hoc fault recovery mechanisms, the system and method described herein employs a global fault response which enables a CRMD to consistently recover from transient faults while maintaining a history of the reason for the device fault. System resets are generated within the device by either software or hardware as the global fault response. Upon detection of a fault, the primary controller signals the reset controller which then issues a reset command. All sub-systems of the primary device controller are then reset together rather than resetting individual sub-systems independently to ensure deterministic behavior. In an exemplary embodiment, described in greater detail below, a primary device controller providing full-capability diagnostics and therapy in the device is interfaced to a reset controller which manages the reset process. A fail-safe sub-system, referred to below as a safety core, is an optional secondary system that can provide limited therapy as backup while the reset process proceeds. Prior to issuing the reset command, the reset controller causes primary device operation to halt, enables a back-up therapy subsystem, causes the primary controller to log the failure condition prior to initiation of the reset process. However, if the fault interferes with the ability of the device to perform logging, the reset process will occur unconditionally. The activation of the back-up therapy subsystem also occurs unconditionally, independent of the success or failure of the logging process. During the reset process, the primary therapy system executes a complete self-test and re-initialization, to ensure that the primary system is functioning correctly, before returning control to that component. If the self-test fails, the device remains on the back-up therapy subsystem.

1. Exemplary Implantable Device Description

Implantable cardiac rhythm management devices such as pacemakers and cardioverter/defibrillators are battery-powered devices which are usually implanted subcutaneously on the patient's chest and connected to electrodes by leads threaded through the vessels of the upper venous system into the heart. FIG. 1 illustrates an implantable device 105 which may be, for example, a pacemaker capable of delivering bradycardia, resynchronization and/or anti-tachycardia pacing, an implantable cardioverter/defibrillator, or a combination pacemaker/defibrillator. The device is equipped with one or more other leads 110 having electrodes incorporated therein for sensing cardiac electrical activity and/or delivering electrical stimulation to the heart. The leads 110 are adapted to be intra-vascularly disposed in an accessible location of the venous system or within a heart chamber. For example, lead/electrodes may be disposed in the right atrium, right ventricle and in a cardiac vein for sensing cardiac activity and/or delivering pacing pulses to the right atrium, right ventricle, and left ventricle, respectively. The device 105 includes a hermetically sealed housing 130, formed from a conductive metal, such as titanium. Housing 130 (also referred to as a "case" or "can") may be substantially covered over its entire surface by a suitable insulator, such as silicone rubber, except for at a window that forms a third electrode, referred to as a "case" or "can" electrode. A header 140, which may be formed of an insulating material, is mounted on housing 130 for receiving the leads 110. The leads 110 are routed through a sealed feedthrough and connected to electronic circuitry 135 contained within the housing 130 which generates pacing pulses or shock pulses in response to sensed cardiac activity. An electrode can be incorporated into a sensing channel that generates an electrogram signal representing cardiac electrical activity at the electrode site and/or incorporated into a pacing or shocking channel for delivering pacing or shock pulses to the site. A pacing channel is made up of a pulse generator connected to an electrode while a sensing channel is made up of a sense amplifier connected to an electrode. A MOS switch matrix may be used to switch the electrodes from the input of a sense amplifier to the output of a pulse generator as well as allow the sensing and pacing channels to be configured by the controller with different combinations of the available electrodes.

Figure 2:
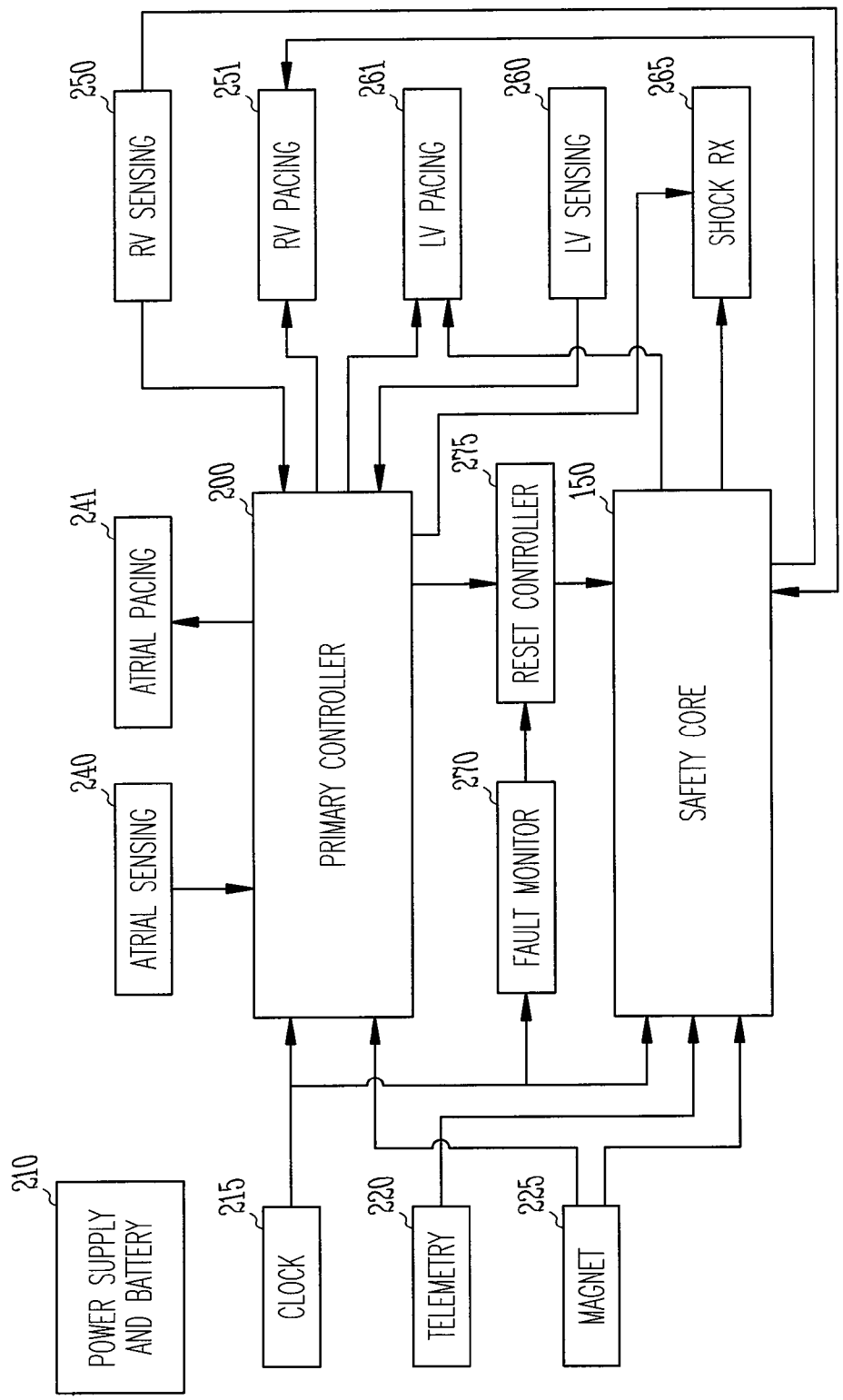
FIG. 2 is a system diagram of exemplary electronic circuitry used to deliver therapy and recover from system faults.

The components of electronic circuitry 135 are illustrated in FIG. 2. A primary controller 200 is made up of a microprocessor and associated memory for program and data storage. The primary controller 200 and other electronic circuitry is powered by a battery and power supply 210. A clock 215 generates timing pulses which drive the controller 200 and other hardware timers of the device. A telemetry system 220 is also provided which enables the controller 200 to communicate with an external device such as an external programmer via a wireless telemetry link. Another means for communication with the device is provided by magnetically actuated switch 225 which is interfaced to the controller 200 and actuated when a magnet is placed in proximity to the device.

The primary controller 200 controls the overall operation of the device in accordance with programmed instructions stored in memory, including controlling the delivery of paces via the pacing channels, interpreting sense signals received from the sensing channels, and implementing timers for defining escape intervals and sensory refractory periods. The pulse generator circuit of each pacing channel is interfaced to the controller 200 so that the output of pacing pulses is under program control. The sensing circuit of each sensing channel is interfaced to the controller and includes a sense amplifier connected to an electrode and a threshold comparator. In FIG. 2, three sensing circuits 250, 240, and 260 are provided for sensing the right ventricle, the right atrium, and the left ventricle, respectively. Three pulse generator circuits 251, 241, and 261 are provided for pacing the right ventricle, the right atrium, and the left ventricle, respectively. A shock pulse generator 265 is also interfaced to the controller to enable delivery of a cardioversion/defibrillation shock. A sensing circuit detects a chamber sense when an electrogram signal (i.e., a voltage sensed by an electrode representing cardiac electrical activity) generated by a particular channel exceeds a specified intrinsic detection threshold. A chamber sense may be either an atrial sense or a ventricular sense depending on whether it occurs in an atrial or a ventricular sensing channel. Pacing algorithms used in particular pacing modes employ such senses to trigger or inhibit pacing. By measuring the intervals between chamber senses, the device is also able to determine an atrial or ventricular rate, and deliver therapy in the form of a cardioversion/defibrillation shock or anti-tachycardia pacing if a tachyarrhythmia is detected.

The primary controller 200 constitutes the primary control system of the device for providing diagnostics and therapy. Also provided as part of the electronic circuitry 135 are components for enabling fault detection and recovery. A fault monitoring circuit 270 detects various kinds of faults and may include, for example, a watchdog timer, a clock deviation monitor, and circuitry for detecting memory errors. The primary controller 200 may also detect faults related to either the hardware or program execution. When a fault is detected by either the primary controller or the fault monitoring circuit, an input signifying the fault event is provided to reset controller 275. As described below, the reset controller manages the reset process in response to the fault and enables operation of safety core 150. The safety core 150 is a hardware-based fail-safe sub-system for controlling the operation of the device in delivering certain types of therapies when the primary controller is halted due to a system fault. For example, the safety core 150 may provide basic pacing therapy, tachyarrhythmia detection, and shock delivery using hardware-based logic which operates independently from the primary controller.

2. System Reset Process

Figure 3:
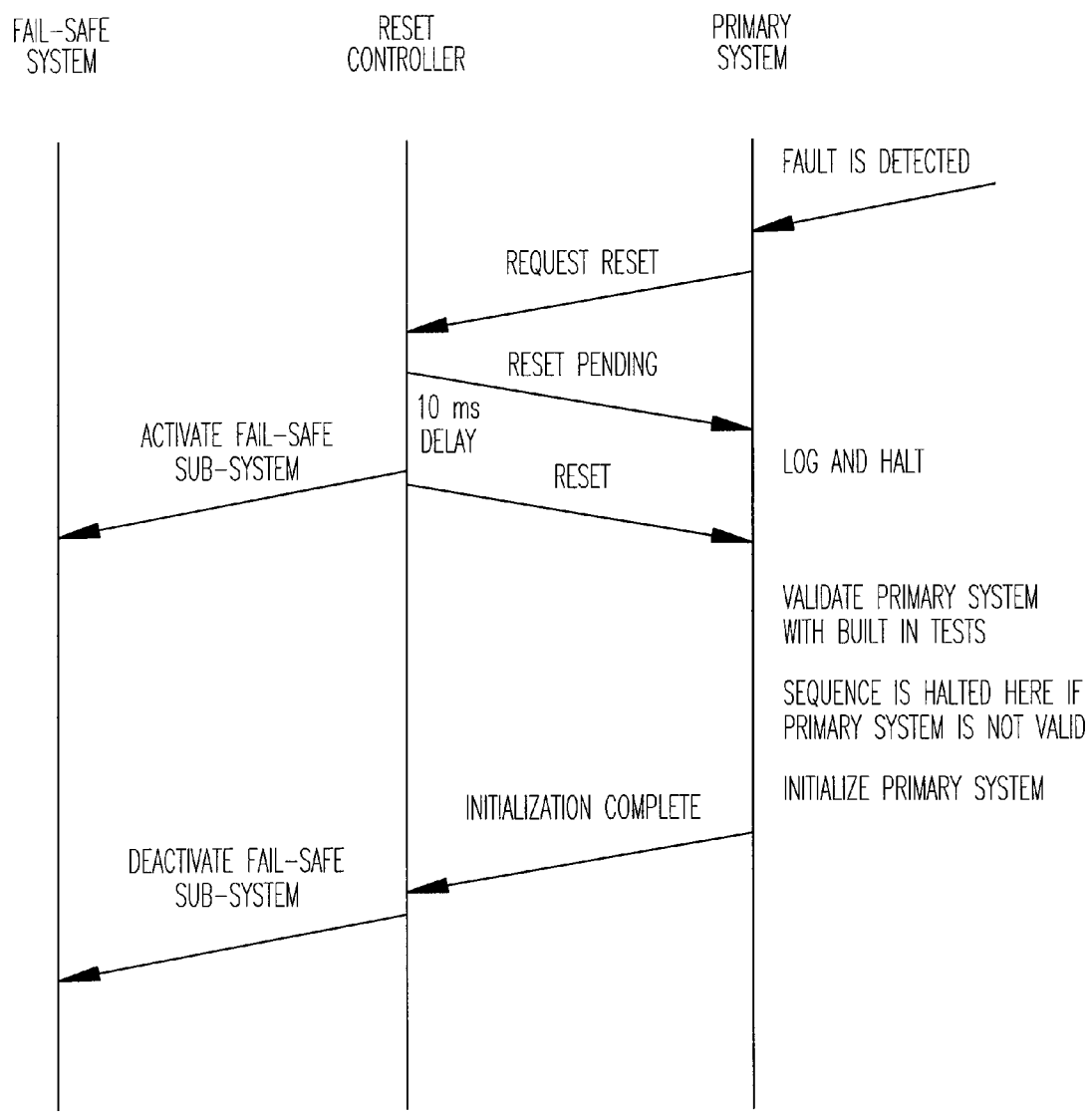
FIG. 3 illustrates an exemplary reset sequence.

The reset sequence, as illustrated by FIG. 3 is initiated when the primary controller 200 or the fault monitoring circuitry 270 detects a fault. A system reset is then requested from the reset controller 275. A pending reset signal is raised by the reset controller to initiate logging of the cause of the pending reset by the primary controller along with context information for later analysis. All therapy functions being performed by the primary controller are halted at this time to prevent further abnormal behavior. A delay (e.g., on the order of 10 milliseconds) ensues to allow the logging, operation to complete. This time is arbitrarily chosen and may be adjusted within reason to accommodate the logging requirements. The logging operation is performed by the primary controller if possible, but this is not guaranteed as the fault leading to the system reset may be so severe that no further operation is possible. A reset signal is subsequently raised to the primary system to initiate built-in self-tests used to validate the primary system. The fail-safe subsystem, if one exists, is reset and activated by the reset controller 275 to continue providing service as needed by the device. If the system is validated, the primary system is allowed to re-initialize and resume operation. When the initialization process has successfully completed, the reset controller deactivates the fail-safe sub-system.

The operation of the reset controller may be optionally modified to provide improved tolerance to system faults by incorporating a system-reset monitor which detects system resets caused by non-recoverable and persistent faults. The system-reset monitor provides a mechanism to bound repeated system resets that may occur as a result of faults that are not corrected by system resets and helps to prevent denial of therapy due to non-recoverable and persistent faults. As described above, either software or hardware within the device may generate internal resets which are used to reset the system in an attempt to recover from a transient fault. Telemetry from external equipment may generate resets, referred to as external resets. In this embodiment, a reset count maintained by the system-reset monitor is incremented when an internal reset occurs and is cleared by an external reset. The reset count is decremented by one count every 48 hours (or other specified time period), where the 48 hour time period starts from the first reset and stops when the reset count is zero. Since many system tests are executed daily, this allows faults that occur daily to eventually trip the monitor. The 48 hour time period also provides some margin for delay of daily tests.

A non-recoverable or persistent fault is detected when a specified number (e.g., three) of internal resets occur within a 48-hour period. When a non-recoverable or persistent fault is detected, the system-reset monitor inhibits further attempts to restart the primary system and allows the fail-safe backup system to maintain therapy indefinitely without interruption. The system-reset monitor logs the three most recent resets in a FIFO buffer. As the reset count is decremented, the oldest logged event is deleted, and external resets clear the entire buffer. The logged resets may be interrogated with telemetry. The system-reset monitor is disabled once it has tripped to prevent subsequent internal resets from overwriting data and is re-enabled with an external reset.

3. Backup Defibrillation Therapy

As aforesaid, a fail-safe subsystem may be provided as part of the fault recovery system in order to allow limited device operation in providing therapy when the primary controller is halted during the reset process or if the primary controller is unable to recover from the fault. The safety core 150 may be configured to provide treatment of cardiac tachyarrhythmia events in the presence of system faults which prevent tachyarrhythmia therapy from being delivered by the primary controller 200. Common circuitry is used to both independently monitor therapy delivery from the primary system as well as provide therapy when the primary system has failed. The safety core defibrillator is implemented in hardware logic rather than firmware logic executed by a processor. This reduces the dependency on the correct functioning of all of the components needed to make firmware operate, increasing the reliability of this safety function. During the system reset or when the primary controller is disabled, the safety core defibrillator is configured to use sense signals generated by the right ventricular sensing circuit in order to detect tachyarrhythmias.

Figure 4:
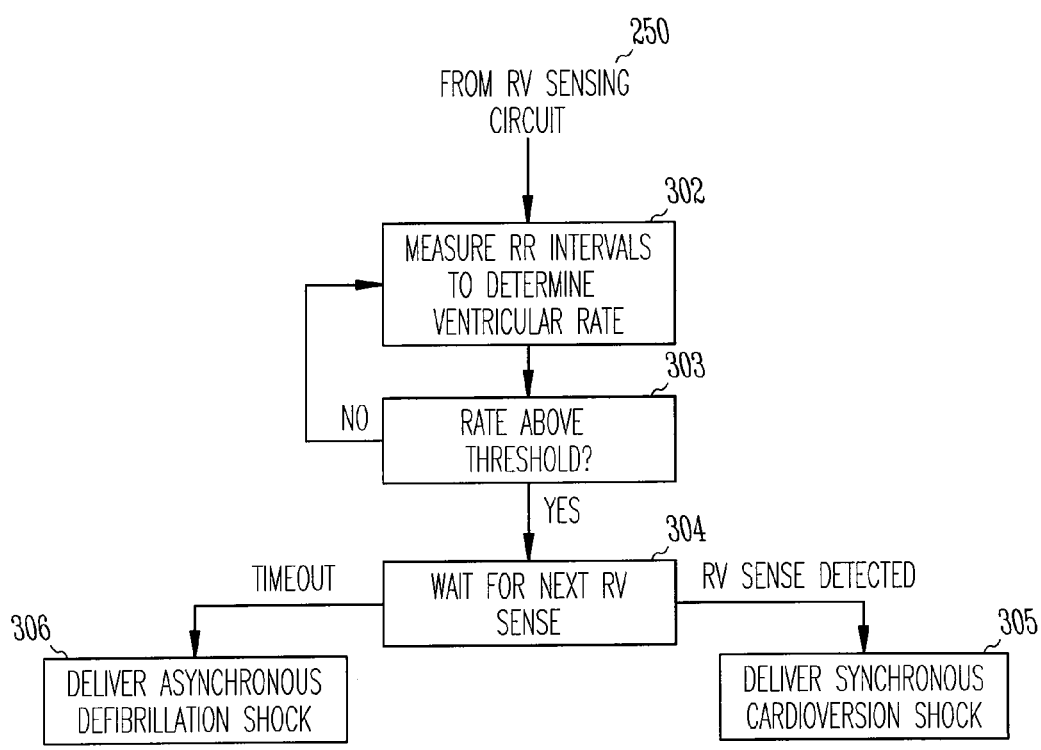
FIG. 4 is a functional block diagram of a safety core defibrillator.

FIG. 4 illustrates a functional block diagram of the safety core defibrillator. RV senses generated by RV sensing circuit 250 are counted by a rate detector at state 302. The rate detector determines the ventricular rate by using the clock signal to measure the intervals between successive RV senses. If the ventricular rate is above a specified threshold for a specified period of time (e.g., 1 second) as determined at state 303, the circuitry waits at state 304 for the next RV sense and then causes the shock pulse generator 265 to deliver a synchronous cardioversion shock at 305. The circuitry also incorporates a timer so that if a predetermined period of time passes without receipt of an RV sense (e.g., 2 seconds), the timer times out and causes delivery of an asynchronous defibrillation shock at 306 by the shock pulse generator 265.

Safety core defibrillator operation is initiated with each system reset. When the primary controller 200 successfully completes its reset sequence, it is responsible for disabling the safety core defibrillator. If non-recoverable or repeated transient system faults occur during the operation of the primary system, control is transferred to the safety core defibrillator. A number of mechanisms may be provided to enable or disable the safety core defibrillator. For example, telemetry may be used to allow a clinician to enable or disable therapy by the safety core defibrillator after the device is implanted. A keyed control register may be provided to allow the primary controller to disable the safety core defibrillator in order to prevent therapy competition. The primary would use this mechanism, for example, after it has successfully completed its initialization. The safety core defibrillator may also be automatically disabled in the event of charge faults during operation to prevent therapy retries when the shock pulse output circuits has been damaged or in the event that the battery capacity is insufficient to delivery therapy. A non-volatile register may be used to provide a priority disable for the safety core defibrillator which may be used, for example, to allow the primary controller to be tested during manufacture. This provides a safe guard preventing dangerous voltages on the output leads during manufacture. In another embodiment, when a magnet is detected by actuation of magnetic switch 225, therapy delivery by the safety core defibrillator is immediately inhibited. After the magnet has been applied for a period of time (e.g. 1 second), the therapy may be diverted and further detection of tachyarrhythmias inhibited until the magnet is removed. In one embodiment, the magnet must then be removed for a period of time (e.g., 2 seconds) in order to allow detection to continue.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A system for providing tachyarrhythmia therapy in the presence of a system fault, comprising:
    a ventricular sensing circuit;
    a shock pulse generator;
    a primary controller for controlling the operation of the shock pulse generator;
    fault monitoring circuitry;
    a safety core defibrillator which is configured to be activated upon detection of a system fault which initiates a system reset and halts the primary controller;
    wherein the safety core defibrillator is a hardware-based logic circuit which measures the intervals between successive ventricular senses and causes the shock pulse generator to deliver a shock pulse if the ventricular rate is above a specified threshold; and, wherein the safety core defibrillator is configured to be automatically disabled in the event of charge faults during operation in order to prevent therapy retries when the shock pulse output circuits has been damaged or in the event that the battery capacity is insufficient to delivery therapy.

2. The system of claim 1 wherein the primary controller is halted when a fault is detected.

3. The system of claim 1 wherein, during a system reset or when the primary controller is halted, the safety core defibrillator is configured to use sense signals generated by a right ventricular sensing circuit in order to detect tachyarrhythmias.

4. The system of claim 3 wherein the safety core defibrillator comprises a rate detector which determines the ventricular rate by using a clock signal to measure the intervals between successive RV senses.

5. The system of claim 4 further wherein the safety core defibrillator comprises a shock controller and shock pulse generator and further wherein the safety core defibrillator operates such that if the ventricular rate is above a specified threshold for a specified period of time the shock controller is activated which waits for the next RV sense and then causes the shock pulse generator to deliver a synchronous cardioversion shock.

6. The system of claim 5 wherein the shock controller incorporates a timer so that if a predetermined period of time passes without receipt of an RV sense, the timer times out and causes delivery of an asynchronous defibrillation shock by the shock pulse generator.

7. The system of claim 1 wherein the primary controller disables the safety core defibrillator when the primary controller successfully completes its reset sequence.

8. The system of claim 1 further comprising a keyed control register to allow the primary controller to disable the safety core defibrillator in order to prevent therapy competition.

9. The system of claim 1 further comprising a reset controller for managing a reset process after detection of a fault by the fault monitoring circuitry.

10. The system of claim 9 wherein, upon detection of a fault, the reset controller is configured to signal the primary controller to halt operation and initiate logging of possible causes of the fault and to activate the safety core defibrillator.

11. The system of claim 9 wherein, upon detection of a fault, the reset controller is configured to signal the primary controller to validate its operation with a self-test and to deactivate the safety core defibrillator if the primary controller is validated.

12. The system of claim 9 wherein, upon detection of a fault, a pending reset signal is raised by the reset controller to initiate logging of the cause of the pending reset by the primary controller.

13. The system of claim 1 wherein the fault monitoring circuitry includes a watchdog timer.

14. The system of claim 1 wherein the fault monitoring circuitry includes a clock deviation monitor.

15. The system of claim 1 wherein the fault monitoring circuitry includes circuitry for detecting memory errors.

16. The system of claim 1 wherein the primary controller may detect faults related to either hardware or program execution.

17. The system of claim 1 further comprising a system-reset monitor for detecting system resets caused by non-recoverable and persistent faults.

18. A system for providing tachyarrhythmia therapy in the presence of a system fault, comprising:

a ventricular sensing circuit;

a shock pulse generator;

a primary controller for controlling the operation of the shock pulse generator;

fault monitoring circuitry;

a safety core defibrillator which is activated upon detection of a system fault which initiates a system reset and halts the primary controller;

wherein the safety core defibrillator is a hardware-based logic circuit which measures the intervals between successive ventricular senses and causes the shock pulse generator to deliver a shock pulse if the ventricular rate is above a specified threshold; and, a non-volatile register to provide a priority disable for the safety core defibrillator.

19. A system for providing tachyarrhythmia therapy in the presence of a system fault, comprising:

a ventricular sensing circuit;

a shock pulse generator;

a primary controller for controlling the operation of the shock pulse generator;

fault monitoring circuitry;

a safety core defibrillator which is activated upon detection of a system fault which initiates a system reset and halts the primary controller;

wherein the safety core defibrillator is a hardware-based logic circuit which measures the intervals between successive ventricular senses and causes the shock pulse generator to deliver a shock pulse if the ventricular rate is above a specified threshold; and, a magnetic switch and wherein, when a magnet is detected by actuation of the magnetic switch, therapy delivery by the safety core defibrillator is immediately inhibited.

* * * * *